(12) United States Patent
Yang et al.

(10) Patent No.: US 9,693,680 B2
(45) Date of Patent: Jul. 4, 2017

(54) VISION TESTING APPARATUS AND METHOD

(71) Applicant: BOE TECHNOLOGY GROUP CO., LTD., Beijing (CN)

(72) Inventors: Li Yang, Beijing (CN); Yefei Dong, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 99 days.

(21) Appl. No.: 14/750,366

(22) Filed: Jun. 25, 2015

(65) Prior Publication Data

US 2016/0270652 A1  Sep. 22, 2016

(30) Foreign Application Priority Data

Mar. 19, 2015 (CN) .......................... 2015 1 0123017

(51) Int. Cl.
*A61B 3/10* (2006.01)
*A61B 3/032* (2006.01)
*A61B 3/06* (2006.01)
*A61B 3/00* (2006.01)

(52) U.S. Cl.
CPC ............ *A61B 3/032* (2013.01); *A61B 3/0075* (2013.01); *A61B 3/0325* (2013.01); *A61B 3/066* (2013.01)

(58) Field of Classification Search
CPC ....... A61B 5/742; A61B 5/7475; A61B 3/032; A61B 5/743; A61B 17/1626; A61B 5/103; A61B 3/103; A61B 3/022; A61B 3/066; A61B 3/152; A61B 3/1208
USPC .................. 351/211, 212, 221, 246, 239, 222
See application file for complete search history.

(56) References Cited

U.S. PATENT DOCUMENTS

| | | | | |
|---|---|---|---|---|
| 5,436,681 A | * | 7/1995 | Michaels | ............. A61B 3/0325 351/239 |
| 5,568,209 A | * | 10/1996 | Priester | .................. A61B 3/032 351/239 |
| 5,801,809 A | | 9/1998 | Husain | |
| 6,379,007 B1 | | 4/2002 | Farb | |
| 2015/0085258 A1 | | 3/2015 | Ichikawa et al. | |

FOREIGN PATENT DOCUMENTS

| | | |
|---|---|---|
| CN | 1077873 A | 11/1993 |
| CN | 1473019 A | 2/2004 |
| CN | 101375788 A | 3/2009 |
| TW | 201429444 A | 8/2014 |
| WO | 2013/157573 A1 | 10/2013 |

OTHER PUBLICATIONS

Second Chinese Office Action in Chinese Application No. 201510123017.0 mailed May 3, 2016 with English translation.
Chinese Office Action of Chinese Application No. 201510123017.0, mailed Dec. 1, 2015 with English translation.

* cited by examiner

*Primary Examiner* — Hung Dang
(74) *Attorney, Agent, or Firm* — Collard & Roe, P.C.

(57) ABSTRACT

Embodiments of the present disclosure relate to a field of vision testing technique, and particularly to a vision testing apparatus and method. The vision testing method and apparatus can concurrently test vision and ability for distinguishing colors concurrently by using vision synthetic-testing pictures, wherein a character in the vision synthetic-testing picture is used to test the vision, and color combination in the vision synthetic-testing picture is used to test the ability for distinguishing colors.

17 Claims, 8 Drawing Sheets

VISION TESTING APPARATUS AND METHOD

CROSS REFERENCE TO RELATED APPLICATIONS

This application claims priority under 35 U.S.C. §119 of Chinese Application No. 201510123017.0 filed on Mar. 19, 2015, the disclosure of which is incorporated by reference.

TECHNICAL FIELD OF THE DISCLOSURE

The present disclosure relates to a field of vision testing technique, and particularly to a vision testing apparatus and method.

BACKGROUND

At present, during vision testing, a vision testing table is commonly adopted to test vision, and color-blindness testing pictures are then adopted to test ability for distinguishing colors, testing conclusion for a tested subject can be obtained only after multiple times of tests have been performed.

It is troublesome and time-consuming for the subject to obtain the vision and the ability for distinguishing colors. In addition, currently, it is necessary for a medical personnel to provide an instruction to the subject at any time during the vision testing for the subject determining direction of a character that the medical personnel instructs, which takes up more medical staff, increases burden on the medical staff, and also increases error rate caused by human factors.

SUMMARY

In embodiments of the present disclosure, there is provided a vision testing apparatus and method capable of testing vision and ability for distinguishing colors concurrently.

According to an aspect of the embodiments of the present disclosure, there is provided a vision testing apparatus comprising: a display unit configured to display a vision synthetic-testing picture; a controller configured to receive a vision testing feedback of a tested subject to the vision synthetic-testing picture and transmit the vision testing feedback to a processing unit; the processing unit configured to generate a vision judgment result based on the vision testing feedback, wherein a character in the vision synthetic-testing picture is used to test the vision, and color combination in the vision synthetic-testing picture is used to test the ability for distinguishing colors.

According to the embodiments of the present disclosure, the vision judgment result is a vision testing result of the tested subject or information indicating a next vision synthetic-testing picture to be displayed, wherein the information indicating the next vision synthetic-testing picture to be displayed comprises picture information and color combination information of the next vision synthetic-testing picture to be displayed.

According to the embodiments of the present disclosure, the vision testing apparatus further comprises: a picture calling unit configured to receive the picture information of the next vision synthetic-testing picture to be displayed, call vision testing picture information corresponding to the picture information of the next vision synthetic-testing picture to be displayed, and transmit the vision testing picture information to the display unit, the picture information comprising information of characters in the next vision synthetic-testing picture to be displayed for testing vision; and a color calling unit configured to receive the color combination information of the next vision synthetic-testing picture to be displayed, call the vision testing color combination corresponding to the color combination information of the next vision synthetic-testing picture to be displayed, and transmit the vision testing color combination to the display unit, wherein the display unit displays the next vision synthetic-testing picture to be displayed according to the vision testing picture and the vision testing color combination.

According to the embodiments of the present disclosure, the controller is a handle controller. Optionally, buttons or joystick can be arranged on the handle controller and can be used to input vision testing feedback.

Optionally, the color combination of the vision synthetic-testing picture is any one of red and green combination, purple and brown combination, red and brown combination, and red, green, grey and purple combination.

According to another aspect of the present disclosure, there is provided a vision testing method comprising concurrently test vision and ability for distinguishing colors concurrently by using vision synthetic-testing pictures. A character in the vision synthetic-testing picture is used to test the vision, and color combination in the vision synthetic-testing picture is used to test the ability for distinguishing colors.

According to the embodiments of the present disclosure, said concurrently testing vision and ability for distinguishing colors by using vision synthetic-testing pictures comprises: displaying a vision synthetic-testing picture; receiving a vision testing feedback of a tested subject to the vision synthetic-testing picture; generating a vision judgment result based on the vision testing feedback.

According to the embodiments of the present disclosure, the vision judgment result is a vision testing result of the tested subject or information indicating a next vision synthetic-testing picture to be displayed, wherein the information indicating the next vision synthetic-testing picture to be displayed comprises picture information and color combination information of the next vision synthetic-testing picture to be displayed.

According to the embodiments of the present disclosure, said concurrently testing vision and ability for distinguishing colors by using vision synthetic-testing pictures comprises: receiving the picture information and the color combination information of the next vision synthetic-testing picture to be displayed; calling the vision testing picture information corresponding to the picture information of the next vision synthetic-testing picture to be displayed; calling the vision testing color combination information corresponding to the color combination information of the next vision synthetic-testing picture to be displayed.

Optionally, the next vision synthetic-testing picture to be displayed and the displayed vision synthetic-testing picture have a same vision level or different vision levels.

Optionally, the color combination of the vision synthetic-testing picture is any one of red and green combination, purple and brown combination, red and brown combination, and red, green, grey and purple combination.

According to the embodiments of the present disclosure, in case that the vision detecting feedback coincides with the displayed vision synthetic-testing picture, the vision judgment result is information of a vision synthetic-testing picture having a vision level being one-level higher than that of the displayed vision synthetic-testing picture.

According to the embodiments of the present disclosure, in case that the vision detecting feedback coincides with the displayed vision synthetic-testing picture for two or three times continuously, the vision judgment result is information of a vision synthetic-testing picture having a highest vision level in a vision testing table.

According to the embodiments of the present disclosure, in case that the vision detecting feedback does not coincide with the displayed vision synthetic-testing picture, the vision judgment result is information of a vision synthetic-testing picture having a vision level being one-level lower than that of the displayed vision synthetic-testing picture.

According to the embodiments of the present disclosure, in case that the vision detecting feedback does not coincide with the displayed vision synthetic-testing picture for two or three times continuously, the vision judgment result is information of a vision synthetic-testing picture having a lowest vision level in a vision testing table.

According to the embodiments of the present disclosure, in case that the displayed vision synthetic-detecting picture has a color combination different from the black and write combination and the vision detecting feedback does not coincide with the displayed vision synthetic-testing picture, the next vision synthetic-detecting picture to be displayed has a same vision level in the vision detecting table as that of the displayed vision synthetic-detecting picture and has the black and write combination.

According to the embodiments of the present disclosure, in case that the displayed vision synthetic-testing picture has a black and write combination and the vision detecting feedback does not coincide with the displayed vision synthetic-testing picture, the next vision synthetic-detecting picture to be displayed has a vision level being one-level lower than that of the displayed vision synthetic-testing picture and has the black and write combination.

According to the embodiments of the present disclosure, in case that the displayed vision synthetic-testing picture has a lowest vision level in the vision testing table and has a black and write combination and the vision detecting feedback coincides with the vision synthetic-detecting picture, the next vision synthetic-detecting picture to be displayed has a vision level being one-level higher than the lowest vision level in the vision detecting table and has the black and write combination.

According to the embodiments of the present disclosure, in case that the displayed vision synthetic-testing picture has a vision level being one-level higher than the lowest vision level in the vision detecting table and has the black and write combination and the vision detecting feedback does not coincide with the displayed vision synthetic-detecting picture, the next vision synthetic-detecting picture to be displayed has the lowest vision level in the vision detecting table and has a color combination different from the black and write combination.

According to the embodiments of the present disclosure, the vision synthetic-detecting picture initially displayed has a vision level of 0.6 or 2.0 in the vision detecting table.

According to the vision testing apparatus and method of the embodiments of the present disclosure, it is convenient to test the vision and the ability of distinguishing colors of the tested subject concurrently, thus avoiding troublesome caused by separate testing of the vision and the ability of distinguishing colors, saving time for detecting, and decreasing the burden on the medical staff.

Optionally, the vision level refers to a vision level in the vision testing table and commonly is a vision level of 0.1, 0.15, 0.2, 0.3, 0.4, 0.6, 0.8, 1.0, 1.2, 1.5 or 2.0. The bigger the value of the vision level is, the smaller the characters in the corresponding vision testing picture are, and the higher the vision is.

BRIEF DESCRIPTION OF THE DRAWINGS

In order to explain the technical solutions in the embodiments of the present disclosure or in the prior art more clearly, accompanying drawings required for describing the embodiments of the present disclosure or the prior art will be introduced. Obviously, the accompanying drawings below are only some embodiments of the present disclosure, and based on the accompanying drawings, other accompanying drawings can be obtained by those skilled in the art without paying inventive labor.

FIGS. 10-1, 10-2, 10-3, 10-4, 10-5, 10-6, 10-7, 10-8, 10-9, 10-10 and 10-11 are schematic diagrams of vision levels in a vision level testing table in prior art.

DETAILED DESCRIPTION

Descriptions will be made clearly and thoroughly for the technical solutions in the embodiments of the present disclosure below, taken in conjunction with the accompanying drawings of the embodiments of the present disclosure. Obviously, the described embodiments are only some but not all of the embodiments of the present disclosure. Other embodiments obtained by those skilled in the art based on the described embodiments without paying inventive labor shall belong to the scope sought for protection in the present disclosure.

Below, a vision testing apparatus and method according to embodiments of the present disclosure will be described in detail with reference to the accompanying drawings.

Figure 1:
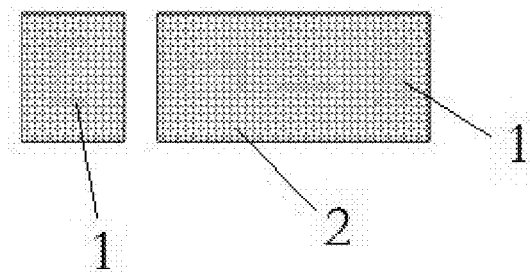
FIG. 1 is a vision synthetic-testing picture with a red and green combination displayed on a vision testing apparatus according to an embodiment of the present disclosure.
Figure 2:
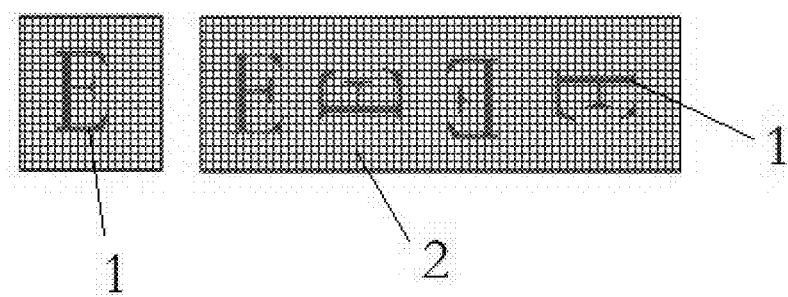
FIG. 2 is a vision synthetic-testing picture with a purple and brown combination displayed on a vision testing apparatus according to an embodiment of the present disclosure.
Figure 3:
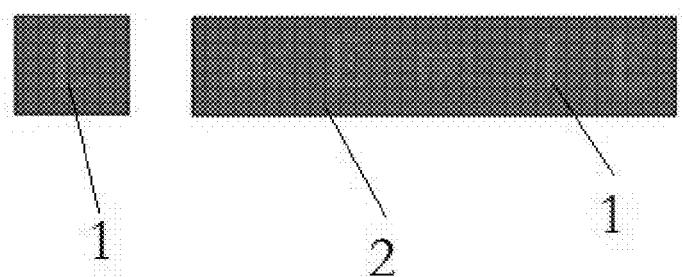
FIG. 3 is a vision synthetic-testing picture with a red and brown combination displayed on a vision testing apparatus according to an embodiment of the present disclosure.

The vision testing apparatus according to the embodiment of the present disclosure adopts vision synthetic-testing pictures to test vision and ability for distinguishing colors. Examples of the vision synthetic-testing pictures are as shown in FIGS. 1-3. Particularly, character 1 in the vision synthetic-testing picture is used to test the vision, and color combination in the vision synthetic-testing picture is used to test the ability for distinguishing colors.

The character 1 may be characters in a vision testing table in prior art, for example "E", "C", "⊥" and so on. Particular size of the character 1 may depend on a vision level corresponding thereto in the vision testing table. The vision level may commonly be 0.1, 0.15, 0.2, 0.3, 0.4, 0.6, 0.8, 1.0, 1.2, 1.5 or 2.0, as shown in FIGS. 10-1, 10-2, 10-3, 10-4, 10-5, 10-6, 10-7, 10-8, 10-9, 10-10 and 10-11. The bigger the value of the vision level is, the smaller the character in the corresponding vision testing picture is, and the higher the vision is. The character in the vision synthetic-testing picture may be a single character, or may be a plurality of characters of a same vision level, or may be a plurality of characters corresponding to a plurality of vision levels. Of course, characters, size of the characters and number of the characters may be set properly according to different requirements.

The color combination of the vision synthetic-testing picture refers to the color combination of the character 1 and character background 2. Particular color combination scheme can refer to color-blindness testing pictures in prior art. Difference lies in that size of characters in the vision synthetic-testing picture is further used for testing the vision level. Generally, the color combination may be red and green combination, purple and brown combination, red and brown combination, or red, green, grey and purple combination used to test ability for distinguishing red and green colors, ability for distinguishing purple and brown colors, ability for distinguishing red and brown colors, or ability for distinguishing red, green, grey and purple colors, respectively. Particularly, for example, the character 1 is red and the character background 2 is green, as shown in the vision synthetic-testing picture with the red and green combination in FIG. 1; or the character 1 is purple and the character background 2 is brown, as shown in the vision synthetic-testing picture with the purple and brown combination in FIG. 2; or the character 1 is red and the character background 2 is brown, as shown in the vision synthetic-testing picture with the red and brown combination in FIG. 3. Alternatively, the character 1 is green and the character background 2 is red, which can also be used to test the ability for distinguishing red and green colors; or the character 1 is brown and the character background 2 is purple, which can also be used to test the ability for distinguishing purple and brown colors; or the character 1 is brown and the character background 2 is red, which can also be used to test the ability for distinguishing red and brown colors. In actual application, the color combination of the vision synthetic-testing picture may also be set as other different color combinations. If the ability of the tested subject for distinguishing colors is low, the color combination of the vision synthetic-testing picture may be set as black and write combination. In this case, the vision level is tested at first, and the ability for distinguishing colors is then tested.

According to the embodiment of the present disclosure, the vision and the ability for distinguishing colors of the tested subject may be tested concurrently by using the vision synthetic-testing pictures, thus avoiding troublesome caused by separate testing of the vision and the ability of distinguishing colors, saving time for detecting, and decreasing the burden on the medical staff.

Figure 4:
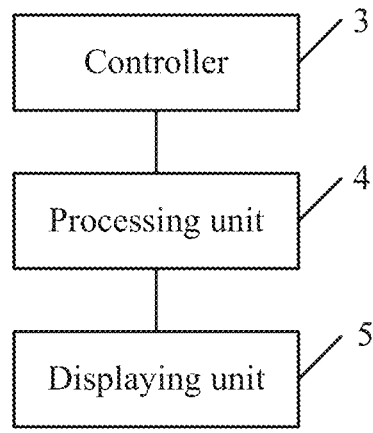
FIG. 4 is a schematic diagram of a vision testing apparatus according to an embodiment of the present disclosure.

As shown in FIG. 4, the vision testing apparatus according to the embodiment of the present disclosure comprises: a display unit 7, a controller 3 and a processing unit 4.

The display unit 7 is configured to display a vision synthetic-testing picture. The controller 3 is configured to receive a vision testing feedback of a tested subject to the vision synthetic-testing picture and transmit the vision testing feedback to the processing unit 4. The processing unit 4 is configured to generate a vision judgment result based on the vision testing feedback, wherein a character in the vision synthetic-testing picture is used to test the vision, and color combination in the vision synthetic-testing picture is used to test the ability for distinguishing colors.

According to the embodiments of the present disclosure, the vision judgment result is a vision testing result of the tested subject or information indicating a next vision synthetic-testing picture to be displayed, wherein the information indicating the next vision synthetic-testing picture to be displayed comprises picture information and color combination information of the next vision synthetic-testing picture to be displayed.

The tested subject views the vision synthetic-testing picture displayed on the display unit 7, and provides the vision testing feedback to the vision synthetic-testing picture displayed on the display unit 7 to the controller 3. The controller 3 receives the vision testing feedback, and transmits the vision testing feedback to the processing unit 4. The processing unit 4 receives the vision testing feedback and generates the vision judgment result based on the vision testing feedback.

Particularly, the processing unit 4 compares the vision testing feedback with the vision synthetic-testing picture displayed on the display unit, so as to generate the vision judgment result. Optionally, in case that the vision testing feedback coincides completely with direction of the character in the vision synthetic-testing picture displayed on the display unit, the processing unit may determine that the tested subject clearly sees the direction of the character in the vision synthetic-testing picture displayed on the display unit; and in case that the vision testing feedback does not coincide completely with the direction of the character in the vision synthetic-testing picture displayed on the display unit (that is, there is at least one mismatching between the vision testing feedback and the direction of the character in the displayed vision synthetic-testing picture), the processing unit may determine that the tested subject cannot see the direction of the character in the vision synthetic-testing picture displayed on the display unit.

In case that the processing unit can determine the vision testing result of the tested subject based on the vision testing feedback, the vision judgment result is the vision testing result of the tested subject. In case that the processing unit cannot determine the vision testing result of the tested subject based on the vision testing feedback, the vision judgment result is the information indicating a next vision synthetic-testing picture to be displayed. The judgment criterion whether the processing unit can determine the vision testing result of the tested subject based on the vision testing feedback may be any judgment in the prior art, and no limitation is made here.

Optionally, if the processing unit 4 generates the vision testing result of the tested subject, the medical personnel may determine whether to continue testing based on the vision testing result. If the processing unit 4 generates the information indicating a next vision synthetic-testing picture to be displayed, it is necessary to continue the testing, and the display unit 7 displays the next vision synthetic-testing picture. The operation will be continued until the vision and the ability for distinguishing colors of the tested subject are obtained.

With the vision testing apparatus according to the embodiments of the present disclosure, half-automatic vision testing may be achieved, avoiding that the medical personnel points to the vision testing picture by means of a pointing tool, that the medical personnel gives information related to the vision testing picture to the tested subject intentionally or unintentionally, and that the medical personnel makes man-made error when obtaining the vision judgment result based on the vision testing feedback, and thus making the testing result more accurate and decreasing the burden on the medical personnel.

Figure 5:
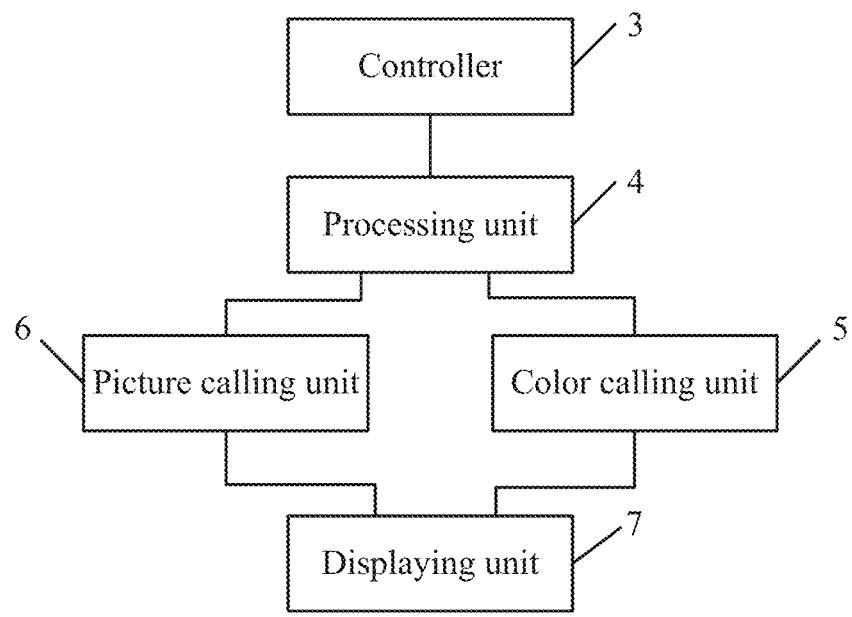
FIG. 5 is a schematic diagram of a vision testing apparatus according to another embodiment of the present disclosure.

As shown in FIG. 5, according to another embodiment of the present disclosure, the vision testing apparatus may further comprise: a picture calling unit 6 and a color calling unit 5.

The picture calling unit 6 is configured to receive the picture information of the next vision synthetic-testing picture to be displayed, call vision testing picture information corresponding to the picture information of the next vision synthetic-testing picture to be displayed, and transmit the vision testing picture information to the display unit 7. The vision testing picture information comprises information of characters for testing vision.

The color calling unit 5 is configured to receive the color combination information of the next vision synthetic-testing picture to be displayed, call vision testing color combination information corresponding to the color combination information of the next vision synthetic-testing picture to be displayed, and transmit the vision testing color combination information to the display unit.

The display unit 7 displays the next vision synthetic-testing picture according to the vision testing picture information and the vision testing color combination information.

The tested subject views the vision synthetic-testing picture displayed on the display unit 7, and provides the vision testing feedback to the vision synthetic-testing picture displayed on the display unit 7 to the controller 3. The controller 3 receives the vision testing feedback, and transmits the vision testing feedback to the processing unit 4. The processing unit 4 receives the vision testing feedback and generates the vision judgment result based on the vision testing feedback. In case that the processing unit 4 generates the information indicating a next vision synthetic-testing picture to be displayed, it is necessary to continue testing, and the picture calling unit 6 and the color calling unit 5 may call and transmit the vision testing picture information and the vision testing color combination information to the display unit 7, respectively. The display unit 7 displays the next vision synthetic-testing picture, and then the tested subject views the next vision synthetic-testing picture displayed on the display unit 7. The operation will be continued until the vision and the ability for distinguishing colors of the tested subject are obtained.

With the vision testing apparatus according to the embodiment of the present disclosure, the vision and the ability for distinguishing colors can be tested concurrently, and automatic vision testing may be achieved by using the display unit, the controller, the processing unit, the picture calling unit and the color calling unit, avoiding that the medical personnel points to the vision testing picture by means of a pointing tool, that the medical personnel gives information related to the vision testing picture to the tested subject intentionally or unintentionally, and that the medical personnel makes man-made errors when obtaining the vision judgment result based on the vision testing feedback, and thus making the testing result more accurate and decreasing the burden on the medical personnel. Moreover, since the next vision synthetic-testing picture is generated by the vision testing apparatus automatically, the burden on the medical personnel is further decreased.

Figure 6:
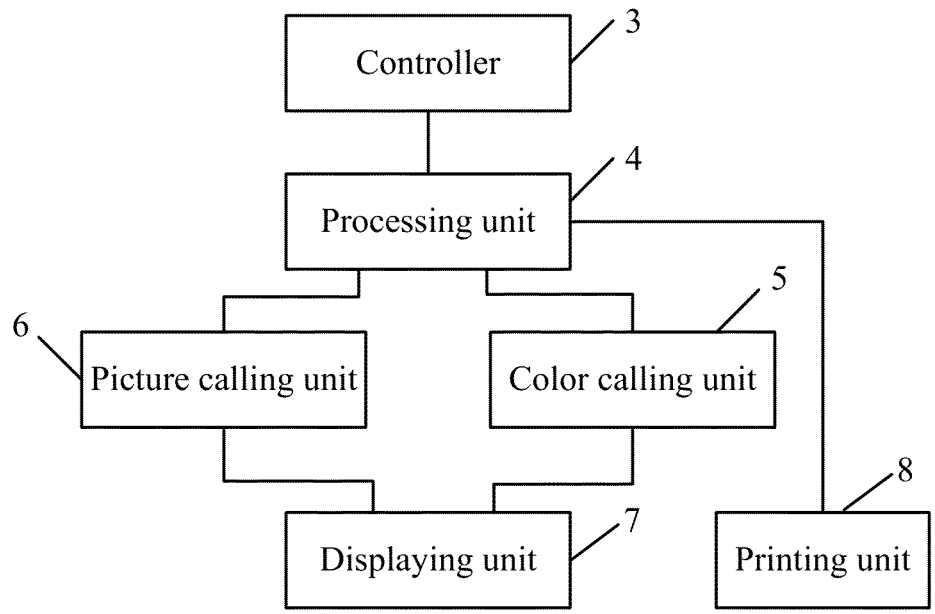
FIG. 6 is a schematic diagram of a vision testing apparatus according to yet another embodiment of the present disclosure.

Preferably, the vision testing apparatus according to the embodiment of the present disclosure further comprises a printing unit 8, as shown in FIG. 6. The printing unit 8 is connected to the processing unit 4 and is configured to print the vision testing result.

The printing unit prints the vision testing result automatically according to the vision testing result information generated by the processing unit, such that the automatic operation of the vision testing apparatus is further improved, thus avoiding the man-made errors caused by operations of the medical personnel, decreasing the burden on the medical personnel, and shortening time for the tested subject to get the testing result.

Optionally, the controller 3 is a handle controller on which buttons or joystick can be arranged for inputting vision testing feedback. The handle controller makes operations of the tested subject more convenient, and the tested subject can input the vision testing feedback through the buttons or joystick of the handle controller. The buttons may be indication buttons such as upward, downward, leftward, and rightward buttons, and may be set as other buttons which may be determined to make the operations of the tested subject more convenient.

In order to test the ability for distinguishing red and green colors, the ability for distinguishing purple and brown colors, the ability for distinguishing red and brown colors, or the ability for distinguishing red, green, grey and purple colors of the tested subject, the color combination of the vision synthetic-testing picture may be red and green combination, purple and brown combination, red and brown combination, or red, green, grey and purple combination. Optionally, the color combination of the vision synthetic-testing picture may be set as red and green combination, purple and brown combination, red and brown combination, and red, green, grey and purple combination sequentially, such that the ability for distinguishing red and green colors, the ability for distinguishing purple and brown colors, the ability for distinguishing red and brown colors, and the ability for distinguishing red, green, grey and purple colors of the tested subject can be tested sequentially.

According to another embodiment of the present disclosure, there is provided a vision testing method capable of testing the vision and the ability for distinguishing colors concurrently by using vision synthetic-testing pictures. A character in the vision synthetic-testing picture is used to test the vision, and color combination in the vision synthetic-testing picture is used to test the ability for distinguishing colors.

Figure 7:
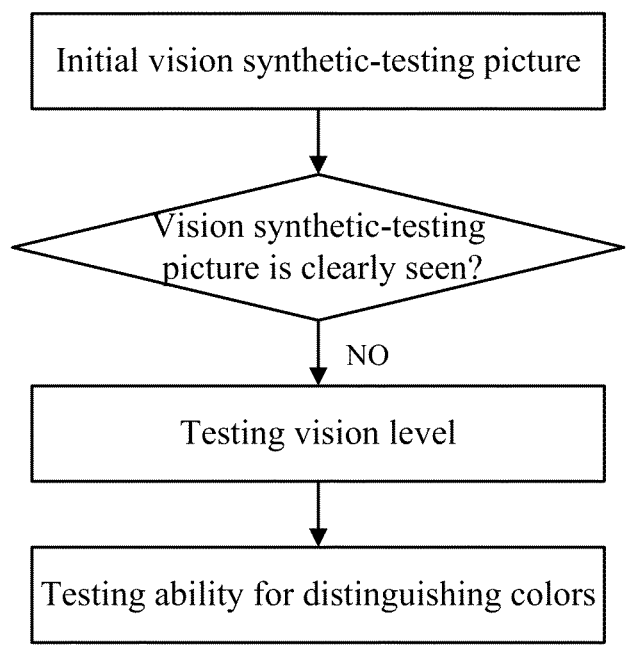
FIG. 7 is a partial flowchart of a vision testing method according to an embodiment of the present disclosure.

In the vision testing method of the embodiment of the present disclosure, as shown in FIG. 7, the vision and the ability for distinguishing colors of the tested subject are tested by means that the tested subject views characters and color combination of an initial vision synthetic-testing picture. In case that the tested subject cannot clearly see characters and/or color combination of the initial vision synthetic-testing picture, it is possible that a vision level corresponding to the initial vision synthetic-testing picture is too high and size of the characters of the initial vision synthetic-testing picture is too small, or that the ability of the tested subject for distinguishing the color combination of the initial vision synthetic-testing picture is low. Under this circumstance, another vision synthetic-testing picture needs to be used to continue testing. Generally, the vision level may be tested at first (judgment criterion may be same as that for the vision level testing in prior art). After the vision level of the tested subject is determined, a set of or several sets of vision synthetic-testing pictures corresponding to the vision level of the tested subject or a set of or several sets of vision synthetic-testing pictures having characters bigger than those in the vision synthetic-testing pictures corresponding to the vision level of the tested subject will be shown for view by the tested subject. The color combination of the vision synthetic-testing pictures may begin with the color combination of the initial vision synthetic-testing picture, such that the ability of the tested subject for distinguishing the color combination of the initial vision synthetic-testing picture will be tested firstly, and then the color combination of the vision synthetic-testing pictures may be set as other color combinations, for example, the color combination of the vision synthetic-testing pictures may be set as red and green combination, purple and brown combination, red and brown combination, and red, green, grey and purple combination and so on (which are different from the color combination of the initial vision synthetic-testing picture) sequentially, such that the ability of the tested subject for distinguishing the red and green combination, purple and brown combination, red and brown combination, and red, green, grey and purple combination will be tested. Of course, other color combinations may be set to be tested in advance, and no requirement is made on the testing sequence of the color combinations only if the ability of the tested subject for distinguishing colors can be tested. Number of the color combinations may be set according to actual requirements, and no limitation is made on the number of the color combinations in this disclosure only if the ability of the tested subject for distinguishing one certain or several color combinations may be finally determined.

Figure 8:
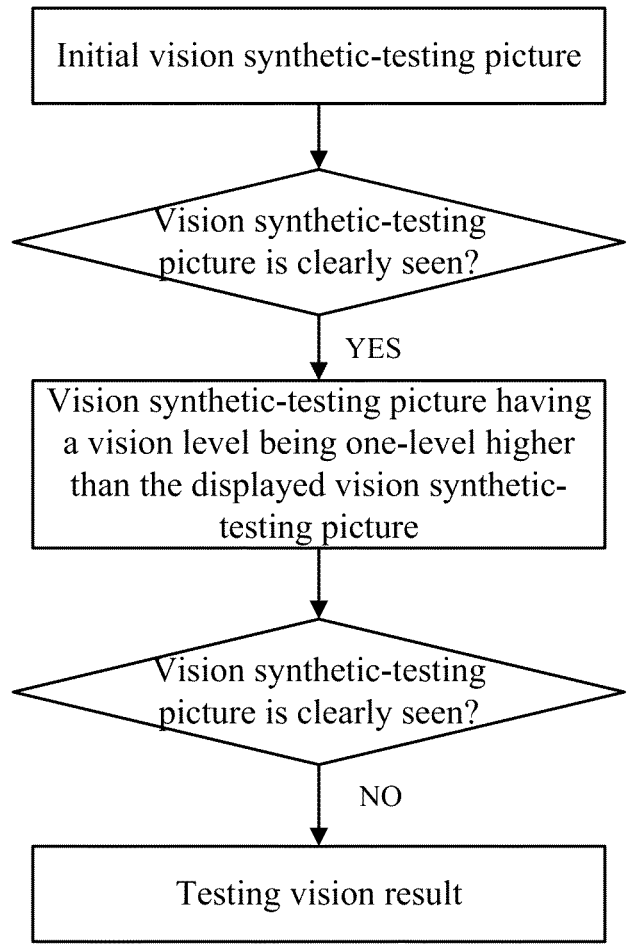
FIG. 8 is a partial flowchart of a vision testing method according to another embodiment of the present disclosure.
Figure 9A:
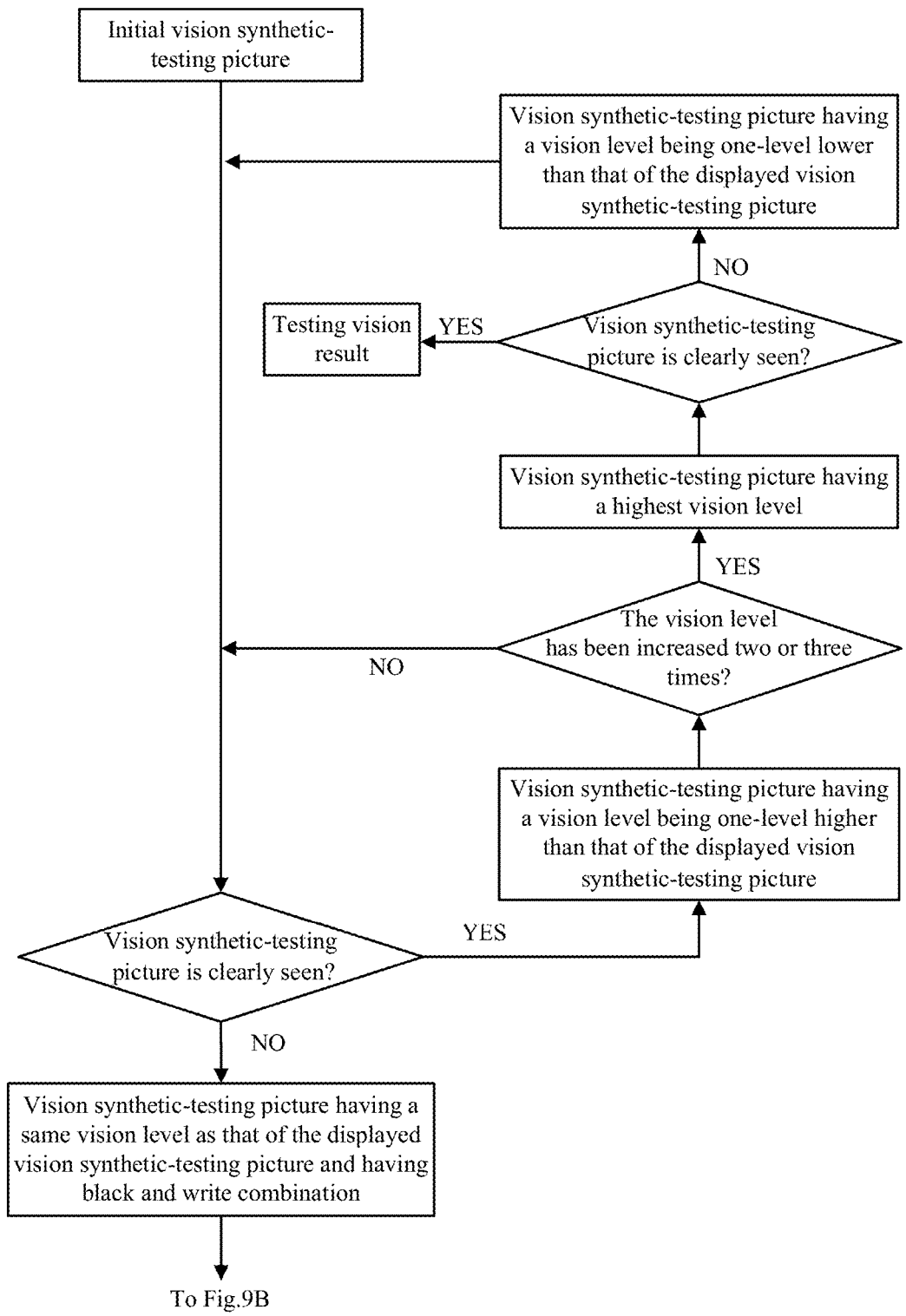
FIG. 9A and FIG. 9B are a partial flowchart of a vision testing method according to yet another embodiment of the present disclosure.
Figure 9B:
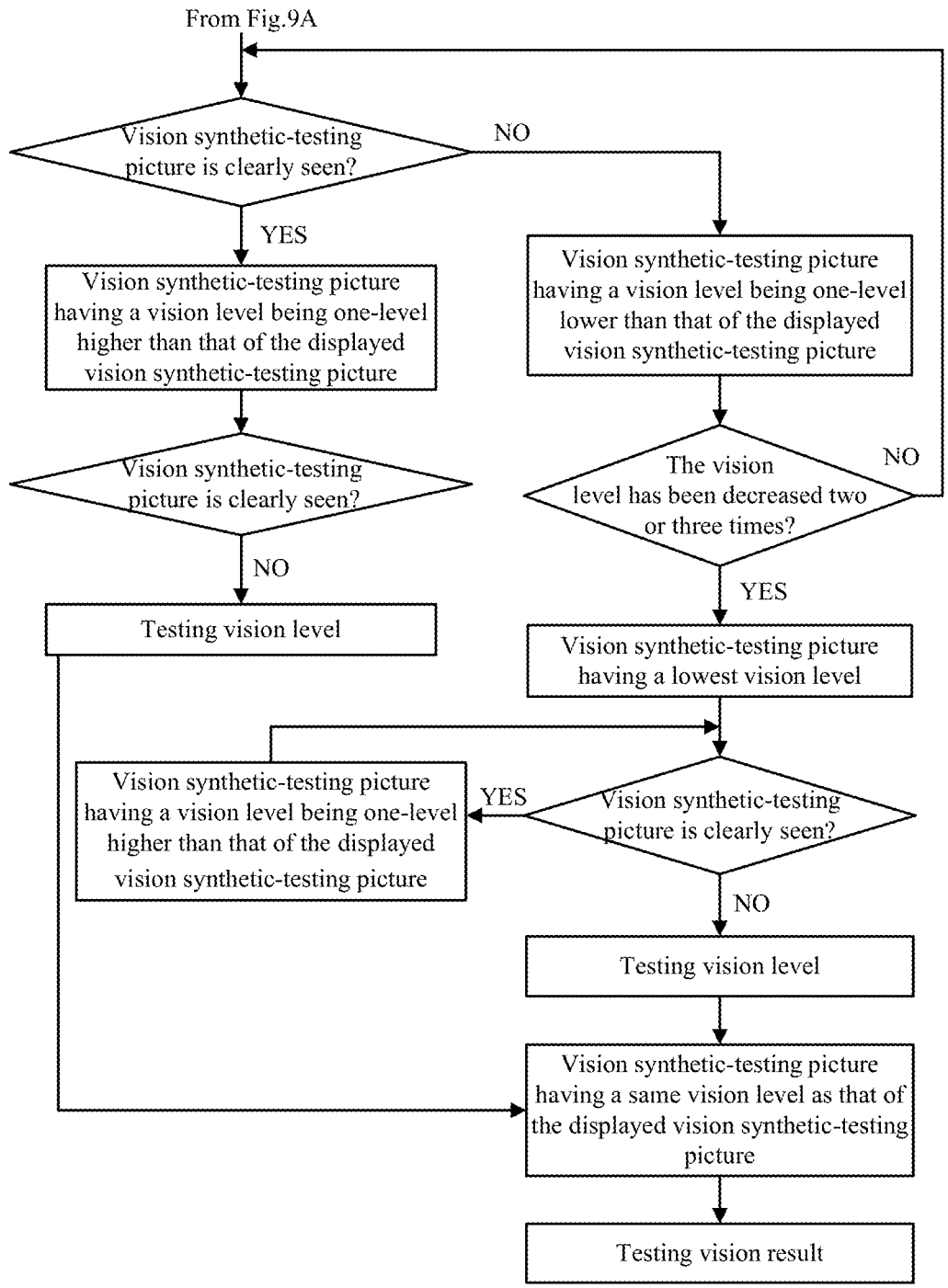

As shown in FIG. 8, if the tested subject can clearly see the characters and the color combination of the initial vision synthetic-testing picture, the next vision synthetic-testing picture to be displayed should be a vision synthetic-testing picture corresponding to a vision level which is one-level higher than the vision level of the initial vision synthetic-testing picture and having the color combination same as that of the initial vision synthetic-testing picture, and the next synthetic-testing picture is displayed on the display unit 7. In case that the tested subject cannot clearly see the next synthetic-testing picture corresponding to the vision level which is one-level higher than the vision level of the initial vision synthetic-testing picture and can clearly see the initial vision synthetic-testing picture, it can be determined that the vision level of the tested subject is the vision level of the initial vision synthetic-testing picture, meanwhile it can be further determined that the tested subject has the ability for distinguishing the color combination of the initial vision synthetic-testing picture.

With the vision testing method according to the embodiment of the present disclosure, the vision and the ability for distinguishing colors may be tested concurrently, which makes testing of the vision and the ability of distinguishing colors of the tested subject more convenient, avoids troublesome caused by separate testing of the vision and the ability of distinguishing colors, saves time for testing, and decreases the burden on the medical staff.

Preferably, the vision testing method comprises the following steps: displaying a vision synthetic-testing picture; receiving a vision testing feedback of a tested subject to the vision synthetic-testing picture; generating a vision judgment result based on the vision testing feedback, wherein a character in the vision synthetic-testing picture is used to test the vision, and color combination in the vision synthetic-testing picture is used to test the ability for distinguishing colors.

Particularly, at step S1, a vision synthetic-testing picture A is displayed on the display unit; at step S2, the controller receives the vision testing feedback of the tested subject to the vision synthetic-testing picture A and transmits the vision testing feedback to the processing unit; at step S3, the processing unit performs judgment processing on the vision testing feedback; and at step S4, the processing unit generates the vision judgment result according to result of the judgment processing. The vision judgment result may be a vision testing result of the tested subject or information indicating a next vision synthetic-testing picture to be displayed, wherein the information indicating the next vision synthetic-testing picture to be displayed comprises picture information and color combination information of the next vision synthetic-testing picture to be displayed.

It is set in advance that the vision synthetic-testing picture A is initially displayed on the display unit, that is, the vision synthetic-testing picture A is the initial vision synthetic-testing picture. The vision synthetic-testing picture A may be a vision synthetic-testing picture corresponding to any vision level in the vision testing table, and the color combination of characters and character background in the vision synthetic-testing picture A may be set according to actual requirements. For easy to perform testing, the vision synthetic-testing picture A may commonly be a vision synthetic-testing picture corresponding to a medium vision level in the vision testing table, and it is preferable that the vision synthetic-testing picture A has a vision level of 0.6, or has a vision level of 0.4 or 0.8.

In the vision testing method according to the embodiments of the present disclosure, the tested subject views the vision synthetic-testing picture displayed on the display unit, and provides the vision testing feedback to the vision synthetic-testing picture displayed on the display unit to the controller; the controller receives the vision testing feedback, and transmits the vision testing feedback to the processing unit; the processing unit receives the vision testing feedback and generates the vision judgment result based on the vision testing feedback. The vision judgment result may be the vision testing result or information indicating a next vision synthetic-testing picture to be displayed.

If the processing unit generates the vision testing result of the tested subject, the medical personnel may determine whether to continue testing based on the vision testing result. If the processing unit generates the information indicating a next vision synthetic-testing picture to be displayed, it is necessary to continue the testing, and the display unit displays the next vision synthetic-testing picture. The operation will be continued until the vision and the ability for distinguishing colors of the tested subject are obtained.

With the vision testing method according to the embodiments of the present disclosure, half-automatic vision testing may be achieved, avoiding that the medical personnel points to the vision testing picture by means of a pointing tool, that the medical personnel gives information related to the vision testing picture to the tested subject intentionally or unintentionally, and that the medical personnel makes man-made error when obtaining the vision judgment result based on the vision testing feedback, and thus making the testing result more accurate and decreasing the burden on the medical personnel.

In a preferable embodiment, the vision synthetic-testing picture A has a vision level of 2.0. The tested subject views the vision synthetic-testing picture displayed on the display unit, and provides the vision testing feedback to the vision synthetic-testing picture displayed on the display unit to the controller. The controller receives the vision testing feedback, and transmits the vision testing feedback to the processing unit. The processing unit receives the vision testing feedback and generates the vision judgment result based on the vision testing feedback. In case that the vision testing feedback coincides completely with direction of the characters in the vision synthetic-testing picture A, the vision judgment result is the vision testing result, that is, the tested subject has the vision level of 2.0 and has the ability for distinguishing the color combination of the vision synthetic-testing picture A.

Figures 1, 10:
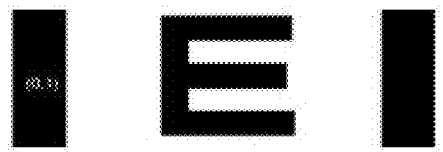
Figures 2, 10:
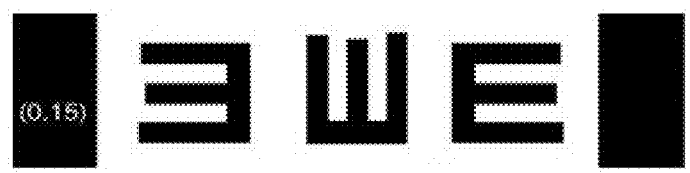
Figures 3, 10:
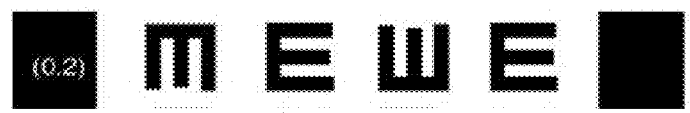
Figures 4, 10:
Figures 5, 10:
Figures 6, 10:
Figures 7, 10:
Figures 8, 10:
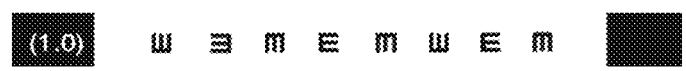
Figures 9, 10:
Figure 10:
Figures 10, 11:
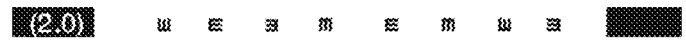

According to another embodiment of the present disclosure, as shown in FIG. 9, the vision synthetic-testing picture A displayed on the display unit has a vision level of 0.6, the tested subject views the vision synthetic-testing picture A displayed on the display unit, and provides the vision testing feedback to the vision synthetic-testing picture A to the controller. The controller receives the vision testing feedback and generates the vision judgment result based on the vision testing feedback. In case that the vision testing feedback does not coincide completely with direction of the characters in the vision synthetic-testing picture A, that is, there is at least one mismatching between the vision testing feedback and the direction of the characters in the vision synthetic-testing picture A, the vision judgment result is the information indicating the next vision synthetic-testing picture to be displayed. The next vision synthetic-testing picture to be displayed may has a vision level of 0.4 or 0.3, or other vision levels lower than 0.6, and has color combination same as that of the vision synthetic-testing picture A. The reason why the tested subject cannot see clearly the direction of characters in the vision synthetic-testing picture A is that the vision level of the vision synthetic-testing picture A is too high and size of the characters of the vision synthetic-testing picture A is too small. In this case, the testing can be performed continuously by using another vision synthetic-testing picture (that is, the next vision synthetic-testing picture) having a vision level which is one-level lower than that of the vision synthetic-testing picture A.

As shown in FIG. 9, the next vision synthetic-testing picture to be displayed may alternatively has a vision level of 0.6 or other vision levels lower than 0.6 (for example, 0.6 in FIG. 9), and has a color combination different from that of the vision synthetic-testing picture A. Preferably, the color combination of the next vision synthetic-testing picture is black and write combination. The reason why the tested subject cannot see clearly the direction of characters in the vision synthetic-testing picture A is that the ability of the tested subject for distinguishing the color combination of the vision synthetic-testing picture A is low. In this case, the testing can be performed continuously by using another vision synthetic-testing picture (that is, the next vision synthetic-testing picture) having a color combination (for example, black and write combination) different from that of the vision synthetic-testing picture A. If the tested subject can clearly see the vision synthetic-testing picture having a vision level of 0.6 and the black and write combination, the next vision synthetic-testing picture to be displayed may have a vision level of 0.8 or other vision levels higher than 0.6 (for example, 0.8 in FIG. 9) and the black and write combination. As shown in FIG. 9, if the tested subject cannot clearly see the vision synthetic-testing picture having the vision level of 0.8, it can be determined that the vision level of the tested subject is 0.6, and the next vision synthetic-testing picture to be displayed should has the vision level of 0.6 and a color combination different from the black and write combination, such that the ability of the tested subject for distinguishing colors can be detected.

As shown in FIG. 9, if the tested subject cannot clearly see the vision synthetic-testing picture having the vision level of 0.6 and the black and write combination, the next vision synthetic-testing picture to be displayed may have a vision level of 0.4 or other vision levels lower than 0.6 and the black and write combination. If the tested subject cannot clearly see the vision synthetic-testing picture, the vision level of which has been decreased two or three times, the next vision synthetic-testing picture to be displayed may have a lowest vision level and the black and write combination. As shown in FIG. 9, if the tested subject can clearly see the vision synthetic-testing picture having the lowest vision level and the black and write combination but cannot clearly see the vision synthetic-testing picture having a vision level being one-level higher than the lowest vision level and the black and write combination, it can be determined that the vision level of the tested subject is the lowest vision level.

As shown in FIG. 9, after the vision level of the tested subject has been determined, it is necessary to display on the display unit other vision synthetic-testing pictures having a vision level same as that of the vision level of the tested subject or having characters which has a size bigger than that of the characters in the vision synthetic-testing picture corresponding to the vision level of the tested subject, such that the ability of the tested subject for distinguishing colors can be determined.

As shown in FIG. 9, if the processing unit determines that the vision testing feedback coincides completely with direction of the characters in the vision synthetic-testing picture A, it generates the information indicating a next vision synthetic-testing picture to be displayed. The next vision synthetic-testing picture to be displayed may have a vision level of 0.8 or other vision levels higher than 0.6. If the tested subject can clearly see the direction of the characters in the vision synthetic-testing picture A and can clearly see the vision synthetic-testing picture, the vision level of which has been increased two or three times continuously, the next vision synthetic-testing picture to be displayed may have a highest vision level. As shown in FIG. 9, if the tested subject can clearly see the vision synthetic-testing picture having the highest vision level, it can be determined that the vision level of the tested subject is the highest vision level 2.0 and the tested subject has the ability for distinguishing the color combination of the vision synthetic-testing picture A. As shown in FIG. 9, if the tested subject cannot clearly see the vision synthetic-testing picture having the highest vision level, the next vision synthetic-testing picture to be displayed may have a vision level being one-level lower than the highest vision level, and the testing needs to be performed continuously.

According to another embodiment of the present disclosure, the vision testing method further comprises: receiving the picture information and the color combination information of the next vision synthetic-testing picture to be displayed; calling the vision testing picture information corresponding to the picture information of the next vision synthetic-testing picture to be displayed; calling the vision testing color combination information corresponding to the color combination information of the next vision synthetic-testing picture to be displayed; transmitting the vision testing picture information and the vision testing color combination information to the display unit; and displaying the next vision synthetic-testing picture on the display unit. The picture information comprises the information concerning characters in the next vision synthetic-testing picture to be displayed.

Particularly, at step S5, the picture calling unit receives the picture information of the next vision synthetic-testing picture to be displayed, calls the vision testing picture information corresponding to the picture information of the next vision synthetic-testing picture to be displayed, and transmits the vision testing picture information to the display unit, the picture information comprises the information concerning characters for testing vision in the next vision synthetic-testing picture to be displayed.

At step S6, the color calling unit receives the color combination information of the next vision synthetic-testing picture to be displayed, calls the vision testing color combination information corresponding to the color combination information of the next vision synthetic-testing picture to be displayed, and transmits the vision testing color combination information to the display unit.

At step S7, the display unit displays the next vision synthetic-testing picture B based on the vision testing picture information and the vision testing color combination information.

Then, the steps S2, S3 and S4 will be performed.

The next vision synthetic-testing picture B and the vision synthetic-testing picture A have a same vision level or different vision levels.

In the vision testing method according to the embodiment of the present disclosure, the tested subject views the vision synthetic-testing picture A displayed on the display unit, and provides the vision testing feedback to the vision synthetic-testing picture A to the controller. The controller receives the vision testing feedback, and transmits the vision testing feedback to the processing unit. The processing unit receives the vision testing feedback and generates the vision judgment result based on the vision testing feedback. In case that the processing unit generates the information indicating the next vision synthetic-testing picture to be displayed, and the picture calling unit and the color calling unit may call and transmit the vision testing picture information and the vision testing color combination information to the display unit, respectively. The display unit displays the next vision synthetic-testing picture B, and then the tested subject views the next vision synthetic-testing picture B displayed on the display unit. The controller receives the vision testing feedback of the tested subject to the next vision synthetic-testing picture B, and transmits the vision testing feedback to the processing unit. The processing unit receives the vision testing feedback and generates the vision judgment result based on the vision testing feedback. The vision judgment result may be a vision testing result of the tested subject or information indicating a next vision synthetic-testing picture to be displayed, wherein the information indicating the next vision synthetic-testing picture to be displayed comprises picture information and color combination information of the next vision synthetic-testing picture.

With the vision testing method according to the embodiment of the present disclosure, the vision and the ability for distinguishing colors can be tested concurrently, and automatic vision testing may be achieved by using the display unit, the controller, the processing unit, the picture calling unit and the color calling unit, avoiding that the medical personnel points to the vision testing picture by means of a pointing tool, that the medical personnel gives information related to the vision testing picture to the tested subject intentionally or unintentionally, and that the medical personnel makes man-made errors when obtaining the vision judgment result based on the vision testing feedback, and thus making the testing result more accurate and decreasing the burden on the medical personnel. Moreover, since the next vision synthetic-testing picture is generated automatically, the burden on the medical personnel is further decreased.

According to a preferable embodiment of the embodiment of the present disclosure, the steps S5, S6, S7, S2, S3 and S4 are performed repeatedly until the processing unit generates the vision testing result. In this way, for tested subjects with different vision conditions, if the vision testing result cannot be obtained after performing the above testing one or two times, the steps S5, S6, S7, S2, S3 and S4 can be performed repeatedly until the processing unit generates the vision testing result, such that the vision level and the ability for distinguishing colors of the tested subject can be determined accurately. Furthermore, the ability for distinguishing a plurality of color combinations of the tested subject can also be determined after the steps S5, S6, S7, S2, S3 and S4 are performed repeatedly.

In order to test the ability of the tested subject for distinguishing red and green combination, purple and brown combination, red and brown combination, or red, green, grey and purple combination, it is preferable that the color combination of the vision synthetic-testing picture is any one of red and green combination, purple and brown combination, red and brown combination, and red, green, grey and purple combination.

In order to provide to the tested subject the vision testing result as soon as possible, it is preferable to print the vision testing result by using the printing unit.

According to another embodiment of the present disclosure, at the step S4, in case that the vision detecting feedback coincides with the vision synthetic-testing picture A, the vision judgment result is information indicating a vision synthetic-testing picture B having a vision level which is one-level higher than the vision synthetic-testing picture A.

Particularly, the vision detecting feedback coincides with the vision synthetic-testing picture A refers to the vision detecting feedback of the tested subject to the vision synthetic-testing picture A completely coincides with the direction of characters in the vision synthetic-testing picture A, which means that the tested subject can clearly see the vision synthetic-testing picture A. To determine the vision condition of the tested subject rapidly and accurately, it is preferable that the vision synthetic-testing picture B has the vision level being one-level higher than that of the vision synthetic-testing picture A.

In a preferable embodiment of the present disclosure, if the steps S5, S6, S7, S2, S3 and S4 are performed repeatedly two or three times and the vision detecting feedback coincides with the displayed vision synthetic-testing picture A in each repeat of the steps S5, S6, S7, S2, S3 and S4, the next vision synthetic-testing picture to be displayed may have a highest vision level in the vision testing table.

Particularly, the vision detecting feedback coincides with the displayed vision synthetic-testing picture A in each repeat of the steps S5, S6, S7, S2, S3 and S4 means that the vision detecting feedback of the tested subject to the vision synthetic-testing picture displayed in the step S7 completely coincides with the direction of characters in the vision synthetic-testing picture displayed in the step S7 in each repeat of the steps S5, S6, S7, S2, S3 and S4. In each repeat of the steps S5, S6, S7, S2, S3 and S4, the vision synthetic-testing picture displayed in the step S7 has a vision level being one-level higher than that of the vision synthetic-testing picture displayed in the last step S7 (that is, the step S7 of its previous repeat), and the vision detecting feedback of the tested subject to the vision synthetic-testing picture displayed in the step S7 completely coincides with the direction of characters in the vision synthetic-testing picture displayed in the step S7, which means that the vision level of the tested subject may relatively high. To determine the vision condition of the tested subject rapidly and accurately, it is preferable that the next vision synthetic-testing picture to be displayed may have the highest vision level in the vision testing table when the steps S5, S6 and S7 are needed to be performed again.

According to another embodiment of the present disclosure, at the step S4, in case that the vision detecting feedback does not coincide with the vision synthetic-testing picture A, the vision judgment result is information indicating a vision synthetic-testing picture B having a vision level which is one-level lower than the vision synthetic-testing picture A.

Particularly, the vision detecting feedback does not coincide with the vision synthetic-testing picture A refers to the vision detecting feedback of the tested subject to the vision synthetic-testing picture A does not completely coincide with the direction of characters in the vision synthetic-testing picture A (that is, there is at least one mismatching between the vision testing feedback and the direction of the characters in the vision synthetic-testing picture A), which means that the tested subject cannot clearly see the vision synthetic-testing picture A. To determine the vision condition of the tested subject rapidly and accurately, it is preferable that the vision synthetic-testing picture B has the vision level being one-level lower than that of the vision synthetic-testing picture A.

In a preferable embodiment of the present disclosure, if the steps S5, S6, S7, S2, S3 and S4 are performed repeatedly two or three times and the vision detecting feedback does not coincide with the displayed vision synthetic-testing picture in each repeat of the steps S5, S6, S7, S2, S3 and S4, the next vision synthetic-testing picture to be displayed may have a lowest vision level in the vision testing table.

Particularly, the vision detecting feedback does not coincide with the displayed vision synthetic-testing picture in each repeat of the steps S5, S6, S7, S2, S3 and S4 means that the vision detecting feedback of the tested subject to the vision synthetic-testing picture displayed in the step S7 does not completely coincide with the direction of characters in the vision synthetic-testing picture displayed in the step S7, that is, there is at least one mismatching between the vision testing feedback and the direction of the characters in the vision synthetic-testing picture displayed in the step S7, in each repeat of the steps S5, S6, S7, S2, S3 and S4. In each repeat of the steps S5, S6, S7, S2, S3 and S4, the vision synthetic-testing picture displayed in the step S7 has a vision level being one-level lower than that of the vision synthetic-testing picture displayed in the last step S7 (that is, the step S7 of its previous repeat), and the vision detecting feedback of the tested subject to the vision synthetic-testing picture displayed in the step S7 does not completely coincide with the direction of characters in the vision synthetic-testing picture displayed in the step S7, which means that the vision level of the tested subject may relatively low. To determine the vision condition of the tested subject rapidly and accurately, it is preferable that the next vision synthetic-testing picture to be displayed may have the lowest vision level in the vision testing table when the steps S5, S6 and S7 are needed to be performed again.

Optionally, the vision synthetic-testing picture A has a color combination different from the black and write combination. At the step S4, it is determined that the vision detecting feedback does not coincide with the displayed vision synthetic-testing picture A, the vision synthetic-testing picture B has a same vision level in the vision testing table as that of the vision synthetic-testing picture A, and the vision synthetic-testing picture B has the black and write combination.

Particularly, the vision detecting feedback does not coincide with the vision synthetic-testing picture A refers to the vision detecting feedback of the tested subject to the vision synthetic-testing picture A does not completely coincide with the direction of characters in the vision synthetic-testing picture A (that is, there is at least one mismatching between the vision testing feedback and the direction of the characters in the vision synthetic-testing picture A), which means that the ability of the tested subject for distinguishing the color combination of the vision synthetic-testing picture A is low, or the vision level of the tested subject is lower than that of the vision synthetic-testing picture A, or the ability of the tested subject for distinguishing the color combination of the vision synthetic-testing picture A is low and the vision level of the tested subject is lower than that of the vision synthetic-testing picture A. To determine the vision condition of the tested subject rapidly and accurately, the vision level of the tested subject may be determined at first and the ability of the tested subject for distinguishing the color combination of the vision synthetic-testing picture A may be then determined. That is, it is preferable that the vision synthetic-testing picture B and the vision synthetic-testing picture A have a same vision level in the vision testing table, and the vision synthetic-testing picture B has the black and write combination, and the vision synthetic-testing picture A has a color combination different from the black and write combination.

According to a preferable embodiment of the present disclosure, if the vision detecting feedback does not coincide with the vision synthetic-testing picture B, the steps S5, S6 and S7 are repeated, and the next vision synthetic-testing picture to be displayed is a vision synthetic-testing picture C has a vision level being one-level lower than the vision synthetic-testing picture B and has the black and write combination.

Particularly, the vision detecting feedback does not coincide with the vision synthetic-testing picture B refers to the vision detecting feedback of the tested subject to the vision synthetic-testing picture B does not completely coincide with the direction of characters in the vision synthetic-testing picture B (that is, there is at least one mismatching between the vision testing feedback and the direction of the characters in the vision synthetic-testing picture B), which means that the tested subject cannot clearly see the vision synthetic-testing picture B. To determine the vision condition of the tested subject rapidly and accurately, it is preferable that the vision synthetic-testing picture C has the vision level being one-level lower than that of the vision synthetic-testing picture B and has the black and write combination.

In a preferable embodiment of the present disclosure, if the steps S5, S6, S7, S2, S3 and S4 are performed repeatedly two or three times and the vision detecting feedback does not coincide with the displayed vision synthetic-testing picture in each repeat of the steps S5, S6, S7, S2, S3 and S4, the next vision synthetic-testing picture to be displayed may have a lowest vision level in the vision testing table when the steps S5, S6 and S7 are needed to be performed for the last time.

Particularly, the vision detecting feedback does not coincide with the displayed vision synthetic-testing picture A in each repeat of the steps S5, S6, S7, S2, S3 and S4 means that the vision detecting feedback of the tested subject to the vision synthetic-testing picture displayed in the step S7 does not completely coincide with the direction of characters in the vision synthetic-testing picture displayed in the step S7, that is, there is at least one mismatching between the vision testing feedback and the direction of the characters in the vision synthetic-testing picture displayed in the step S7, in each repeat of the steps S5, S6, S7, S2, S3 and S4. In each repeat of the steps S5, S6, S7, S2, S3 and S4, the vision synthetic-testing picture displayed in the step S7 has a vision level being one-level lower than that of the vision synthetic-testing picture displayed in the last step S7 (that is, the step S7 of its previous repeat), and the vision detecting feedback of the tested subject to the vision synthetic-testing picture displayed in the step S7 does completely coincide with the direction of characters in the vision synthetic-testing picture displayed in the step S7, which means that the vision level of the tested subject may relatively low. To determine the vision condition of the tested subject rapidly and accurately, it is preferable that the next vision synthetic-testing picture to be displayed may have the lowest vision level in the vision testing table when the steps S5, S6 and S7 are needed to be performed again. The color combination of the next vision synthetic-testing picture with the lowest vision level is commonly the black and write combination.

Preferably, if the vision synthetic-testing picture displayed in the step S7 has the lowest vision level in the vision testing table and the vision testing feedback coincides with the vision synthetic-testing picture displayed in the step S7, the steps S5, S6 and S7 are needed to be performed again, and the next vision synthetic-testing picture to be displayed may have a vision level being one-level higher than the lowest vision level and the black and write combination.

Particularly, the vision testing feedback coincides with the vision synthetic-testing picture displayed in the step S7 means that the vision detecting feedback of the tested subject to the vision synthetic-testing picture displayed in the step S7 completely coincides with the direction of characters in the vision synthetic-testing picture having the lowest vision level displayed in the step S7. In this case, the vision level of the tested subject cannot be determined directly. To determine the vision level of the tested subject accurately, the steps S5, S6 and S7 are needed to be performed again, and the next vision synthetic-testing picture to be displayed may have the vision level being one-level higher than the lowest vision level and has the black and write combination.

If the tested subject can clearly see the vision synthetic-testing picture having the lowest vision level, but cannot clearly see the vision synthetic-testing picture having a vision level being one-level higher than the lowest vision level, it can be determined that the vision level of the tested subject is the lowest vision level. If the tested subject can clearly see the vision synthetic-testing picture having the lowest vision level and can clearly see the vision synthetic-testing picture having a vision level being one-level higher than the lowest vision level, it is necessary to perform the testing continuously.

In a preferable embodiment of the present disclosure, if the vision synthetic-testing picture displayed in the step S7 has the vision level being one-level higher than the lowest vision level in the vision testing table and the vision testing feedback does not coincide with the vision synthetic-testing picture displayed in the step S7, the steps S5, S6 and S7 are needed to be performed again, and the next vision synthetic-testing picture to be displayed is a vision synthetic-testing picture D having the lowest vision level in the vision testing table and not having the black and write combination.

Particularly, the vision testing feedback does not coincide with the vision synthetic-testing picture displayed in the step S7 means that the tested subject can clearly see the vision synthetic-testing picture having the lowest vision level but cannot clearly see the vision synthetic-testing picture having the vision level being one-level higher than the lowest vision level, it can be determined that the vision level of the tested subject is the lowest vision level. That is, the vision level of the tested subject is determined and then the ability of the tested subject for distinguishing colors needs to be determined. To determine the vision condition of the tested subject rapidly and accurately, it is preferable that the vision synthetic-testing picture D has the lowest vision level in the vision testing table and does not have the black and write combination.

If the vision level finally determined is not the lowest vision level, the vision synthetic-testing picture used for testing the ability of the tested subject for distinguishing colors has a vision level same as or lower than that of the tested subject, that is, the ability of the tested subject for distinguishing colors is tested by using the vision synthetic-testing picture comprising characters having a size equal to or bigger than that corresponding to the vision level of the tested subject.

It is preferable that the vision synthetic-testing picture A has the vision level of 0.6 or 2.0 in the vision testing table. The vision level of 0.6 is a medium vision level in the vision testing table. The vision level of most of tested subjects can be determined rapidly and accurately by using an initial vision synthetic-testing picture having the vision level of 0.6. The vision level of tested subjects having relative high vision level can be determined rapidly by using an initial vision synthetic-testing picture having the vision level of 2.0.

The above descriptions are only for illustrating the embodiments of the present disclosure, and in no way limit the scope of the present disclosure. It will be obvious that those skilled in the art may make modifications, variations and equivalences to the above embodiments without departing the spirit and scope of the present disclosure as defined by the following claims. Such variations and modifications are intended to be included within the spirit and scope of the present disclosure.

What is claimed is:

1. A vision testing apparatus comprising:
 a display unit configured to display a vision synthetic-testing picture;
 a controller configured to receive a vision testing feedback of a tested subject to the vision synthetic-testing picture and transmit the vision testing feedback to a processing unit;
 the processing unit configured to generate a vision judgment result based on the vision testing feedback,
 wherein a character in the vision synthetic-testing picture is used to test the vision, and color combination in the vision synthetic-testing picture is used to test the ability for distinguishing colors, the vision judgment result is a vision testing result or information indicating a next vision synthetic-testing picture to be displayed, wherein the information indicating the next vision synthetic-testing picture to be displayed comprises picture information and color combination information of the next vision synthetic-testing picture to be displayed, so as to test vision and ability for distinguishing colors concurrently.

2. The vision testing apparatus of claim 1, further comprising:
 a picture calling unit configured to receive the picture information of the next vision synthetic-testing picture to be displayed, call vision testing picture information corresponding to the picture information of the next vision synthetic-testing picture to be displayed, and transmit the vision testing picture information to the display unit, the picture information comprising information of characters in the vision synthetic-testing picture; and a color calling unit configured to receive the color combination information of the next vision synthetic-testing picture to be displayed, call the vision testing color combination corresponding to the color combination information of the next vision synthetic-testing picture to be displayed, and transmit the vision testing color combination to the display unit, wherein the display unit displays the next vision synthetic-testing picture to be displayed according to the vision testing picture and the vision testing color combination.

3. The vision testing apparatus of claim 1, wherein the controller is a handle controller arranged with buttons or joystick used to input vision testing feedback.

4. The vision testing apparatus of claim 1, wherein the color combination of the vision synthetic-testing picture is any one of red and green combination, purple and brown combination, red and brown combination, and red, green, grey and purple combination.

5. A vision testing method comprising concurrently testing vision and ability for distinguishing colors by using vision synthetic-testing pictures, wherein a character in the vision synthetic-testing picture is used to test the vision, and color combination in the vision synthetic-testing picture is used to test the ability for distinguishing colors, wherein said concurrently testing vision and ability for distinguishing colors by using vision synthetic-testing pictures comprises:

displaying a vision synthetic-testing picture;

receiving a vision testing feedback of a tested subject to the displayed vision synthetic-testing picture; and generating a vision judgment result based on the vision testing feedback, wherein the vision judgment result is a vision testing result or information indicating a next vision synthetic-testing picture to be displayed, wherein the information indicating the next vision synthetic-testing picture to be displayed comprises picture information and color combination information of the next vision synthetic-testing picture to be displayed.

6. The vision testing method of claim 5, wherein said concurrently testing vision and ability for distinguishing colors by using vision synthetic-testing pictures further comprises:

receiving the picture information and the color combination information of the next vision synthetic-testing picture to be displayed, the picture information comprising information of characters in the vision synthetic-testing picture;

calling the vision testing picture information corresponding to the picture information of the next vision synthetic-testing picture to be displayed; and calling the vision testing color combination information corresponding to the color combination information of the next vision synthetic-testing picture to be displayed, wherein the next vision synthetic-testing picture to be displayed and the displayed vision synthetic-testing picture have a same vision level or different vision levels.

7. The vision testing method of claim 6, further comprising:

displaying the next vision synthetic-testing picture according to the vision testing picture information and the vision testing color combination information;

receiving a vision testing feedback of the tested subject to the displayed next vision synthetic-testing picture;

generating another vision judgment result based on the vision testing feedback.

8. The vision testing method of claim 6, wherein in case that the vision detecting feedback coincides with the displayed vision synthetic-testing picture, the vision judgment result is information of a vision synthetic-testing picture having a vision level being one-level higher than that of the displayed vision synthetic-testing picture.

9. The vision testing method of claim 8, wherein in case that the vision detecting feedback coincides with the displayed vision synthetic-testing picture for two or three times continuously, the vision judgment result is information of a vision synthetic-testing picture having a highest vision level in a vision testing table.

10. The vision testing method of claim 6, wherein in case that the vision detecting feedback does not coincide with the displayed vision synthetic-testing picture, the vision judgment result is information of a vision synthetic-testing picture having a vision level being one-level lower than that of the displayed vision synthetic-testing picture.

11. The vision testing method of claim 10, wherein in case that the vision detecting feedback does not coincide with the displayed vision synthetic-testing picture for two or three times continuously, the vision judgment result is information of a vision synthetic-testing picture having a lowest vision level in a vision testing table.

12. The vision testing method of claim 6, wherein in case that the displayed vision synthetic-detecting picture has a color combination different from the black and write combination and the vision detecting feedback does not coincide with the displayed vision synthetic-testing picture, the next vision synthetic-detecting picture to be displayed has a same vision level in the vision detecting table as that of the displayed vision synthetic-detecting picture and has the black and write combination.

13. The vision testing method of claim 6, wherein in case that the displayed vision synthetic-testing picture has a black and write combination and the vision detecting feedback does not coincide with the displayed vision synthetic-testing picture, the next vision synthetic-detecting picture to be displayed has a vision level being one-level lower than that of the displayed vision synthetic-testing picture and has the black and write combination.

14. The vision testing method of claim 6, wherein in case that the displayed vision synthetic-testing picture has a lowest vision level in the vision testing table and has a black and write combination and the vision detecting feedback coincides with the vision synthetic-detecting picture, the next vision synthetic-detecting picture to be displayed has a vision level being one-level higher than the lowest vision level in the vision detecting table and has the black and write combination.

15. The vision testing method of claim 6, wherein in case that the displayed vision synthetic-testing picture has a vision level being one-level higher than the lowest vision level in the vision detecting table and has the black and write combination and the vision detecting feedback does not coincide with the displayed vision synthetic-detecting picture, the next vision synthetic-detecting picture to be displayed has the lowest vision level in the vision detecting table and has a color combination different from the black and write combination.

16. The vision testing method of claim 5, wherein the color combination of the vision synthetic-testing picture is any one of red and green combination, purple and brown combination, red and brown combination, and red, green, grey and purple combination.

17. The vision testing method of claim 5, wherein the vision synthetic-detecting picture has a vision level of 0.6 or 2.0 in the vision detecting table.

* * * * *